(12) United States Patent
Cornelli et al.

(10) Patent No.: US 7,812,005 B2
(45) Date of Patent: *Oct. 12, 2010

(54) GLYCOSAMINOGLYCANS FOR TREATMENT OF EMOTIONAL DYSFUNCTIONS

(75) Inventors: Umberto Cornelli, c/o Cornelli Consulting S.r.l., Corso Indipendenza 1, 20129 Milan (IT); Luigi De Ambrosi, Santhia' (IT); Stanley Lorens, Forest Park, IL (US); Jawed Fareed, Westchester, IL (US); John Lee, Wilmette, IL (US); Israel Hanin, Chicago, IL (US); Ronald Mervis, Columbus, OH (US)

(73) Assignee: Umberto Cornelli, Milan (IT)

( * ) Notice: Subject to any disclaimer, the term of this patent is extended or adjusted under 35 U.S.C. 154(b) by 286 days.

This patent is subject to a terminal disclaimer.

(21) Appl. No.: 10/557,860

(22) PCT Filed: May 19, 2004

(86) PCT No.: PCT/EP2004/050860

§ 371 (c)(1),
(2), (4) Date: Nov. 21, 2005

(87) PCT Pub. No.: WO2004/103381

PCT Pub. Date: Dec. 2, 2004

(65) Prior Publication Data
US 2006/0205690 A1    Sep. 14, 2006

(30) Foreign Application Priority Data
May 21, 2003   (IT)   .......................... MI2003A1023

(51) Int. Cl.
*A61K 31/726*  (2006.01)
*A61K 31/715*  (2006.01)
*A61K 31/727*  (2006.01)
*A61K 31/737*  (2006.01)

(52) U.S. Cl. .............................. 514/54; 514/23; 514/56; 536/123.1

(58) Field of Classification Search .................. 514/54, 514/23, 56; 536/123.1
See application file for complete search history.

(56) References Cited

U.S. PATENT DOCUMENTS
4,956,347 A   9/1990   Ban et al.

FOREIGN PATENT DOCUMENTS
WO   WO 92/21354   12/1992
WO   WO 00/69444   11/2000

OTHER PUBLICATIONS

Ricotti, M.P. (1973) "Benzodiazepine, amitriptilina e antiselerotici nel trattamento di pazienti anziani con psicosi depressive: prove con il test di Hamilton," Riforma Medica 87:1078-1087.
International Search Report from PCT priority application serial No. PCT/EP 2004/050860.
Morgan, C. and Inestrosa, N. C., "Interactions of laminin with the amyloid β peptide. Implications for Alzheimer's disease" *Brazilian Journal of Medical and Biological Research* (2001) 34:597-601.

*Primary Examiner*—Shaojia Anna Jiang
*Assistant Examiner*—Michael C Henry
(74) *Attorney, Agent, or Firm*—Knobbe Martens Olson & Bear LLP

(57) ABSTRACT

The present invention relates to the use of glycosaminoglycan fractions having an average molecular weight of 2400 (±200) D for the preparation of pharmaceutical compositions suitable for the treatment of emotional dysfunctions, especially depressive disorders, anxiety disorders, anxiety neurosis, agitation, confusion.

5 Claims, No Drawings

GLYCOSAMINOGLYCANS FOR TREATMENT OF EMOTIONAL DYSFUNCTIONS

RELATED APPLICATIONS

This application is a U.S. National Phase of International Patent Application No.: PCT/EP2004/050860, filed May 19, 2004, designating the U.S. and published in English on Dec. 2, 2004 as WO 2004/103381, which claims the benefit of priority of Italian Patent Application No.: MI2003A001023, filed May 21, 2003.

FIELD OF THE INVENTION

The invention relates to novel pharmacological applications of glycosaminoglycans, in particular those having an average molecular weight of 2400 (±200) D.

STATE OF THE ART

Emotional disturbances belong to the area of psychiatric illnesses included in depressive, anxiety, psychotic and manic syndromes and are mainly expressed in the form of an abnormal reaction to the surroundings, ranging from aggressiveness, to a state of confusion and to apathy.

Emotional disturbances are treated pharmacologically in various ways depending on their origin. Unipolar affective disorders are treated with tricyclic antidepressants such as imipramine or heterocyclic antidepressants such as selective serotonin uptake inhibitors like fluoxetine, or with monoamine-oxidase inhibitors such as phenelzine (drugs of this type are preferably included in the pharmacology textbook "The pharmacological basis of therapeutics", Chapter 19, X edition 2001).

In contrast, bipolar affective disorders are treated with lithium, valproic acid or other drugs with anticonvulsant action (drugs of this type are preferably included in Chapter 20 of the aforementioned pharmacology textbook).

Primary anxiety disorders, such as generalized anxiety syndromes and obsessive-compulsive syndromes, are treated with the categories of products already mentioned or with benzodiazepines and/or buspirone.

However, all the conditions described have the connotation of syndromes and are defined in the Diagnostic and Statistical Manual of Mental Disorders (Manuale diagnostico e statistics dei disturbi mentali, DMS-IV-R).

Treatment of all of these conditions is strongly recommended and it is considered that about 75% of patients derive clinically significant benefit from them.

Pharmacological treatment of emotional disturbances is, however, accompanied by a number of side effects including, among others, alteration of the normal state of consciousness.

It is considered that certain emotional disturbances, such as aggressiveness, the confusional state and inability to adapt to a new environment, are due to alteration of the extracellular matrix (ECM) in the brain, both in terms of fluidity and of volume, with consequent effects on the brain synapses and on the level of intracerebral transmission (also in terms of volume of transmission).

Therefore products that are able to modify the fluidity and volume of the ECM can be useful for improving intracerebral transmission.

Furthermore, it is known that the glycosaminoglycans have a hyperanxiogenic effect when injected intracerebrally.

SUMMARY OF THE INVENTION

Now, surprisingly, it has been found in vivo that glycosaminoglycans with an average molecular weight of 2400 ($\forall$200) D are able to correct emotional dysfunctions without altering the normal state of consciousness, because of their ability to prevent or reduce the alteration of the extracellular matrix (ECM) in the brain.

Therefore the fraction of glycosaminoglycans having an average molecular weight of 2400 (±200) D can be used for the preparation of pharmaceutical compositions suitable for the treatment of emotional dysfunctions.

DETAILED DESCRIPTION OF THE INVENTION

The present invention therefore relates to the use of a fraction of glycosaminoglycans with an average molecular weight of 2400 (±200) D for the preparation of pharmaceutical compositions capable of preventing or reducing pathologic changes of the extracellular matrix in the brain. Said composition can therefore be used in the treatment of emotional dysfunctions and in particular in depressive disorders, anxiety disorders, anxiety neurosis, agitation and confusion.

As is well known, the glycosaminoglycans (GAGs) are the most abundant heteropolysaccharides in the human body and are made up of repeating units of disaccharides that are formed in their turn from one or two modified sugars N-acetylgalactosamine or N-acetylglucosamine and from a uronic acid, for example glucuronate or iduronate.

The present invention relates in particular to glycosaminoglycan fractions with an average molecular weight of 2400 (±200) D.

Preferably, the GAGs of the present invention are obtained from hyaluronates, dermatan sulphates, chondroitin sulphates, heparin and heparan sulphates, or keratan sulphates.

The said fractions can be produced by depolymerization of the corresponding glycosaminoglycan(s) in various steps comprising: irradiation of the glycosaminoglycan(s) with gamma radiation, followed by gel filtration and ultrafiltration. Methods for obtaining the glycosaminoglycans according to the present invention are known in the art.

According to a particularly preferred embodiment of the present invention, the fractions of GAGs of the present invention are obtained from heparin, for example according to the method described in EP 1181024.

Pharmacological Tests

For pharmacological investigation of the fraction of glycosaminoglycans according to the present invention, an experimental model was applied in the rat for the following evaluations:

1) reaction to the environment, with the "open field" or OF test;
2) learning in the water maze, with the "Morris water maze" (MWM) test;
3) conditioning to a hostile environment, with the "context-dependent fear conditioning" (CDFC) test.

Materials Used in the Experiments

Thirteen Brown Norway (BN) rats were used, obtained from Harlan Sprague-Dawley Inc. (Indianapolis In.) with weight of 300-350 g and age of 11 months.

The animals were adapted to the new environment for two weeks before beginning any treatment or biological test. Assignment to treatment with the drug (7 animals) or with the vehicle alone (6 animals) was randomized. The animals were kept in individual cages and were assessed in accordance with the Association for Assessment and Accreditation of Laboratory Animal Care (AAALAC) in an environment with controlled temperature (22-26° C.) and with circadian light rhythms of 12 h (light starting from 7:00 hours). The animals were given food and water ad libitum. All assessments of behaviour were carried out in a sound-proofed environment next to the living quarters and between the hours of 09:00 and 13:00. At the end of the experiment, i.e. after 42-44 days of treatment with the product under investigation or with the vehicle, the animals were sacrificed with pentobarbital sodium at high dose (100 mg/kg intraperitoneally). All the procedures were approved by the Institutional Animal Care and Use Committee (IAUC) of the Loyala University Medical Center (IACUC).

A glycosaminoglycan fraction with average molecular weight of 2400 (±200) D (identified hereinafter with the symbol C3) was obtained by depolymerization of heparin by gamma-irradiation and successive fractionation to obtain the desired molecular weight, as described in EP 118024, and consisted of a water-soluble white powder. This was dissolved in drinking water at a concentration such that the animals received a daily administration of 25 mg/kg for a period varying between 42 to 44 days. The water consumption of the individual animals was measured during the first two weeks of adaptation. During the experiment, the drinking water containing C3 was renewed every 3-4 days.

The experimental procedure for the analysis of behaviour is shown in the following scheme, subdivided into weeks.

| Week | Procedure |
|------|-----------|
| 1 | Arrival of the animals and adaptation in individual cages |
| 2 | Start of measurement of the amount of water consumed |
| 3 | Start of administration of C3 (25 mg/kg) or of vehicle |
| 5 | Open-field (OF) test - 12 minutes |
| 6–7 | Morris water maze (MWM) Acquisition (6 days) Reversal (3 days) |
| 8 | Context-dependent fear conditioning (CDFC) Adaptation (2 days) Conditioning (3 days) |
| 9 | Sacrifice of the animals |

After two weeks (one of adaptation and one for evaluating the consumption of water) the animals were submitted to the series of three tests:
OF, MWM, CDFC OF (Open Field)

The behaviour resulting from exposure to a new environment (for 12 minutes) permits measurement of a neophobic response (fear of new environments) and of the exploratory response.

The OF test was carried out on a platform with the dimensions 100 cm×100 cm×40 cm high. The walls were constructed of varnished plywood. The floor was painted white and divided into 25 squares (25 cm×25 cm) marked out with a thin black line. In the corners located at the edges of the square formed by the nine central squares of the platform there were four holes 3.5 cm in diameter.

The platform was located in a sound-proofed room with indirect lighting.

The animals were placed at the centre of the platform and were observed for 12 minutes.

Their behaviour was recorded on video cassette. The following behavioural elements were evaluated: 1) the time, in seconds, taken to leave the centre of the square (measurement of fear or initial "freezing") and the time to enter one of the squares alongside the wall (thigmotaxis); 2) the number of squares trod on (horizontal exploration); 3) the number of rearings, i.e. how many times the rat raises itself on its hind legs (vertical exploration); 4) the number of times it puts its snout into one of the holes in the floor.

After each session the OF was washed with a 70% ethanol solution to remove any olfactory stimulus associated with the individual animal.

MWM (Morris Water Maze)

Learning and spatial memory can be evaluated using the water maze, in which the animal's ability to learn and remember the location of a platform that permits it to get out of the water is measured. In addition, the test can evaluate the state of excitation or sedation of the animals.

The maze was constructed from a plastic cylinder (152 cm in diameter and 74 cm high) painted white, filled with water to a height of 56 cm and divisible into quadrants. Half-way between the centre and the edge, 1.5 [cm] below the surface of the water, there was a 9 $cm^2$ platform. The water was made opaque by adding milk powder and its temperature was maintained in the range 22-26° C. The reference points outside the maze were kept constant. The behaviour of each animal was recorded on video (SMART Video Tracking System, San Diego Instruments, San Diego, Calif.). The video camera connected to the computer was situated above the centre of the maze. The computer calculated: 1) the length of the path (cm) taken by the animal to reach the hidden platform; 2) the pause (sec) and the distance (cm) traveled in each quadrant; 3) the latency (sec) for finding and climbing onto the platform.

The animals were submitted to the test 4 times a day. In each test the animals were placed at the edge of the maze. The platform was always located in the same place (quadrant 1) for the first 6 days (learning) and was then put in a different position (quadrant 3) for the "reversal" test carried out on the next three days 7-9.

In the first test the animals were put in quadrant 2, next to the one containing the platform, i.e. quadrant 1. During the next three tests of the day the animals were placed in the adjacent quadrants moving clockwise. The test lasted until the animal reached the platform or up to a maximum of 60 seconds. If the animal did not succeed in reaching the platform in 60 seconds it was gently placed on the platform and left undisturbed for 60 seconds. Each animal was left on the platform for 60 seconds and repeated the test immediately afterwards. At the end of the four tests the animal was gently dried with a towel and put back in its cage.

CDFC (Context-Dependent Fear Conditioning)

This test measures an animal's ability to learn and remember a conditioned stimulus (CS) paired to an adverse unconditional stimulus (UCS).

The test, to be performed in five consecutive days, permits analysis of the animal's ability to learn and remember the relation between events ("foreground") that are conditioned (CS or light) and unconditional (UCS mild electric shock) and the environment ("background").

The animals were adapted to a first environmental context (context A) for two consecutive days.

On the third day the animal's behaviour was analysed during three successive stimuli consisting of light followed by shock (slight passage of current under the paws of moderate intensity but enough to produce pain) which represented the CS and the UCS respectively; these stimuli caused a state of fear that was manifested in the phenomenon of "freezing" (the animal freezes in a characteristic stance) which measured precisely the degree of fear. This sequence of stimuli in fact represents the events called "foreground" that were carried out in context A.

On the fourth day, the animals were put back in context A without any CS or UCS stimulus being produced. This made it possible to analyse the animal's behaviour in "background" (i.e. the environment in which the CS-UCS events previously occurred). Previous experiments indicate that lesions of the hippocampus involve the total inability to remember that this "background" is associated with the conditioning, i.e. with the "foreground". Complete absence of freezing on the fourth day is indicative of memory dysfunctions; i.e. the animal does not remember the context in which the events occurred.

On the fifth day, the animal was placed in a different environment (context B) and only the light stimulus (CS) was applied, to determine whether the animal remembered that this stimulus represented an event of an adverse nature, independently of the environment (no stimulus of the UCS type was applied in this session). The animal's ability to respond with freezing to this different context indicated that it perceived the negative significance of the light stimulus, which was followed by the painful stimulus.

Contexts A and B were represented by small chambers (48 cm long×25 cm deep×28 cm high). The experiment lasted 8 minutes.

In context A the floor consisted of a grating formed from metal tubes with diameter of 2.5 mm, 10 mm apart (centre-to-centre). The walls of the chamber were all of Plexiglass™, the front wall was transparent, that at the rear was black, and the others were white. The 7.5 W lamp for the light stimulus was at the centre of one of the side walls of the chamber, positioned 14 cm from the rear of the chamber.

The "foreground" conditioning of the third day was as follows. After an interval of 2 minutes, the light was switched on (CS) and 20 seconds later an electric shock was applied to the animal's feet ("foot shock"), via the metal grating, lasting 2 seconds with a strength of 0.8 mA of alternating current, supplied from a Grason-Stadler generator, model E1064GS. The animals were submitted to another two sessions of CS and UCS each with an interval of 2 minutes, giving a total of 3 paired CS-UCS. All the sessions were video recorded and evaluated later.

The extent of "freezing" in the four sessions (for a total of 2×4 minutes=8 min/day) was measured in seconds on the basis of the video recordings using a stopwatch.

On the fourth day context A was used again, but the animals were not submitted to any stimulus and therefore the test served for evaluating the response to the background alone, i.e. memory of the hostile environment. Freezing was measured as on the third day.

On the fifth day, context B was used. The chamber dimensions were identical to those in context A. However, the grating and the rear wall were replaced with a plywood panel. The chamber was cleaned using PetZyme™ (which removes colour and odour) immediately after each session. The PetZyme™ causes olfactory stimuli different from those of the 70% ethanol solution used in context A on days 1 to 5. After an interval of two minutes the CS was applied (light for 20 sec) three times with 2-minute intervals. No UCS was applied. Therefore the fifth day served for measuring the foreground conditioning, i.e. the association between environment and hostility. Freezing was measured as on the third day.

Statistical analysis of the data was based on calculating the mean values and the standard error (SE) whereas comparisons between the two groups were made using nonparametric statistics (Mann-Whitney "U" test).

Results

The amount of fluid consumed daily by the animals was 35.7±1.1 ml and the C3 had no effect on this consumption.

Open Field

1) Time to leave the centre (seconds): mean±SE (standard deviation)
(horizontal exploration)
Controls 25.0±8.0
C3 12.6±2.5
U test: p<0.05
2) Total number of squares trod on: mean±SE
Controls 56.5±3.4
C3 76±8.4
U test: p<0.05

These results show that treatment with C3 reduces fear of the environment and as a consequence increases the animals' exploratory attitude.

MWM (Morris Water Maze)

With regard to this test, no noteworthy differences were observed between treated animals and control animals. Both the profile of acquisition and that of "reversal" turned out to be superimposable (data not reported). Since the evaluation of this test is based both on the path length and on the time taken to reach the platform, it can be stated that C3 does not alter learning or motility and therefore does not exert any stimulating action. In other words the animals treated with C3 exhibit neither sedation nor stimulation.

CDFC (Context-Dependent Fear Conditioning)

| 1) Freezing time (seconds): mean ± SE in the 4 sessions on day 3 | | |
|---|---|---|
| | Freezing time | |
| Session | C3 | Controls |
| 1 | 6 ± 2.7 | 5 ± 1.1 |
| 2 | 30 ± 5.0* | 48 ± 3.7 |
| 3 | 61 ± 8.5* | 88 ± 1.8 |
| 4 | 77 ± 9.0* | 86 ± 6.4 |

*U test: p < 0.05

The results show that C3 significantly reduces freezing in all the sessions where the CS and UCS stimuli were applied, indicating an action on the foreground, consisting of reduction of panic when faced with the hostile environment.

2) As indicated in the method, on the fourth day of CDFC the animals were placed in the test chamber for a period of 8 minutes in which the sessions of 2 minutes each did not envisage any stimulus.

In these conditions, however, the animal tends to connect the environment (background) with the memory of the hostile events (foreground) and therefore develops the fear condition.

The results are shown in the following table.

| Freezing time (seconds): mean ± SE in the 4 sessions on day 4 | | |
|---|---|---|
| | Freezing time | |
| Session | C3 | Controls |
| 1 | 23 ± 7.6* | 60 ± 9.5 |
| 2 | 76 ± 11.2 | 94 ± 9.1 |
| 3 | 69 ± 9.9 | 80 ± 6.5 |
| 4 | 70 ± 6.4 | 84 ± 9.2 |

*U test: p < 0.05

The mean values of those treated with C3 in the first session are significantly more reduced relative to those of the controls, a general indicator of a more controlled fear when faced with a hostile environment. In the last sessions the differences between groups no longer remain and the increase in freezing times settles at values that are not significantly different between the two groups, indicating that in both groups there is still the memory of an environment that had been hostile.

3) The results for the fifth day, i.e. when the environmental context is changed and only the light stimulus is applied but not the painful stimulus (thus in absence of the grating), are presented in the following table.

Freezing time (seconds): mean ± SE in the sessions on day 5

| Session | Freezing time | |
|---|---|---|
| | C3 | Controls |
| 1 | 18 ± 6.2 | 12 ± 4.0 |
| 2 | 90 ± 4.0 | 74 ± 5.3 |
| 3 | 110 ± 4.5 | 80 ± 12.0* |
| 4 | 110 ± 4.2 | 106 ± 6.2 |

*U test: $p < 0.05$

The results show that the freezing behaviour is similar in the two groups, i.e. there is a steady increase in both groups. In the group treated with C3 there is an attenuation of freezing which is significantly different from zero at the sixth minute as well as being basically more reduced in the entire session.

CONCLUSIONS

Treatment with C3, at a dose of 25 mg/kg/day for a period of 42-44 days, shows the following effects.

1) Reduction in the OF emotive response and increase in exploration.
2) Reduction in freezing during the CDFC in the acquisition period (day 3), attenuation of it on exposure to the hostile environment alone though without producing hostility (day 4) and finally attenuation of it on exposure in a similar new context and with partial stimuli (day 5). All these three elements, in particular that relating to the period of acquisition, are unambiguous indicators of better adaptation to the environment and to its possible hostility.
3) No impairment of learning and spatial memory in the condition and in the phases (learning and reversal) that can be assessed by means of the water maze.
4) Absence of CNS stimulating or depressing effects that can be revealed by changes in motor activity.

Therefore, the results obtained demonstrate that C3 improves the emotional response to the environment without acting as a CNS depressant or stimulant.

The glycosaminoglycans with an average molecular weight of 2400 (±200) D can therefore be used for the preparation of pharmaceutical compositions that are suitable for the treatment of emotional dysfunctions.

The said compositions include a pharmaceutically effective quantity of the active principle together with pharmaceutically acceptable diluents or excipients and can be in forms that are suitable for subcutaneous, intramuscular, intravenous and oral administration.

Examples of pharmaceutically acceptable diluents or excipients are, for example: physiological saline solution, colloidal silica.

The said compositions normally contain a quantity of glycosaminoglycans in the range from 10 mg to 100 mg.

Treatment of emotional dysfunctions comprises administration of approx. 10 mg to 400 mg/day of active principle to the patient.

In particular, administration of 10-50 mg/day is preferred for subcutaneous, intramuscular and intravenous administration, whereas administration of 50-100 mg/day is preferred in the case of oral administration.

The invention claimed is:

1. A method for the treatment of an emotional dysfunction selected from the group consisting of depressive disorders, anxiety disorders, anxiety neurosis, agitation, and confusion, comprising the step of administering to a patient in need a pharmaceutical composition comprising a pharmaceutically effective amount of a glycosaminoglycan fraction having an average molecular weight of 2400 (±200) D in a dosage of 10 to 400 mg/day, wherein said glycosaminoglycan fraction is obtained by depolymerization of dermatan sulfates, chondroitin sulfates, heparin, heparin sulfates or keratin sulfates.

2. The method according to claim 1, wherein said pharmaceutical composition comprises 10 to 100 mg of said glycosaminoglycan fraction.

3. The method according to claim 1, wherein said dosage is 10 to 50 mg/day by the subcutaneous, intramuscular or intravenous route.

4. The method according to claim 1, wherein said dosage is 50 to 100 mg/day by the oral route.

5. The method according to claim 1, wherein said glycosaminoglycan fraction is obtained by depolymerization of heparin.

* * * * *